United States Patent
Lapeyre

(10) Patent No.: US 8,167,842 B2
(45) Date of Patent: May 1, 2012

(54) INTRODUCER APPARATUS WITH CUTTING EDGES

(75) Inventor: Andre C. Lapeyre, Rochester, MN (US)

(73) Assignee: Mayo Foundation for Medical Education and Research, Rochester, MN (US)

(*) Notice: Subject to any disclaimer, the term of this patent is extended or adjusted under 35 U.S.C. 154(b) by 271 days.

(21) Appl. No.: 12/067,512

(22) PCT Filed: Sep. 21, 2006

(86) PCT No.: PCT/US2006/036870
§ 371 (c)(1),
(2), (4) Date: Jul. 24, 2008

(87) PCT Pub. No.: WO2007/035889
PCT Pub. Date: Mar. 29, 2007

(65) Prior Publication Data
US 2009/0254038 A1    Oct. 8, 2009

Related U.S. Application Data

(60) Provisional application No. 60/719,132, filed on Sep. 21, 2005.

(51) Int. Cl.
*A61M 5/178* (2006.01)
(52) U.S. Cl. .......... 604/164.01; 604/164.05; 604/164.06
(58) Field of Classification Search ............ 604/164.01, 604/164.05, 164.06, 264; 606/167, 190
See application file for complete search history.

(56) References Cited

U.S. PATENT DOCUMENTS

| | | | |
|---|---|---|---|
| 5,624,459 A | 4/1997 | Kortenbach et al. | |
| 5,649,941 A * | 7/1997 | Lary | 606/159 |
| 6,719,746 B2 | 4/2004 | Blanco | |
| 6,921,387 B2 | 7/2005 | Camrud | |
| 2004/0093003 A1* | 5/2004 | MacKenzie et al. | 606/190 |

* cited by examiner

*Primary Examiner* — Nicholas Lucchesi
*Assistant Examiner* — Brooke Matney
(74) *Attorney, Agent, or Firm* — Mueting, Raasch & Gebhardt, P.A.

(57) ABSTRACT

An introducer apparatus with a plurality of cutting edges along the outer surface of the distal end of an introducer with a blunt distal end is disclosed. The introducer may be adapted to extend from and be withdrawn into the sheath. The cutting edges may resect tissue located around the insertion site.

20 Claims, 1 Drawing Sheet

INTRODUCER APPARATUS WITH CUTTING EDGES

RELATED APPLICATION

This application is a U.S. National Stage Application of International Application No. PCT/US2006/036870, titled INTRODUCER APPARATUS WITH CUTTING EDGES, filed Sep. 21, 2006, which claims the benefit under 35 U.S.C. §119(e) of U.S. Provisional Patent Application No. 60/719,132 filed on Sep. 21, 2005 and titled INTRODUCER APPARATUS WITH CUTTING EDGES, which are hereby incorporated by reference in their entireties.

The present invention is directed to the field of introducer sheaths. More particularly, the present invention provides an introducer apparatus that includes a sheath and a complementary introducer with multiple cutting edges on an outer surface of the introducer.

The diagnosis and treatment of heart and peripheral vascular disease often involves puncturing an artery or vein (e.g., the femoral artery) to insert a tube-like introducer sheath. The introducer sheath functions as a portal for passing devices into the body and up to the heart or other locations.

The introducer sheath is typically used during percutaneous procedures such as, e.g., angiography, angioplasty, and stent placement. After the procedure, the introducer sheath is removed and the puncture site is managed to control bleeding.

Conventionally, an introducer sheath has a central passageway to accommodate additional instrumentation/devices and is inserted through a skin incision and into the vessel wall (such as, e.g., the renal or femoral artery or vein) so that other instruments/devices can access the interior of the vessel. The introducer sheath can also be inserted into dialysis grafts to provide access to the graft. Introducer sheaths have many different applications, e.g., peripheral, cardiac, neurovascular, etc.

After the introducer sheath is placed, various instruments may be inserted and withdrawn through the passageway of the sheath into the vessel interior, depending on the procedure. Some examples of such instruments may include, e.g., dilators, angioplasty balloon catheters, stent deployment catheters, angiographic instruments, thrombectomy devices, embolization instruments, etc. These instruments typically have an outer diameter close to the internal diameter of the introducer sheath, which means they will usually abut the inside wall of the sheath.

This relatively tight fit may often result in excessive frictional engagement with the inside wall of the sheath. The frictional engagement may cause difficulty in manipulating the instruments and/or dislodgement of the sheath during instrument withdrawal through the passageway in the sheath. Additionally, surgical instrumentation including expandable features (such as inflatable balloons, etc.) often have a smaller diameter when inserted because, e.g., the balloon is tightly wrapped around the catheter. However, after a balloon is inflated inside the vessel and then deflated for withdrawal, it may not be as tightly wrapped as during its initial insertion. Thus, when the balloon catheter is withdrawn through the passageway of introducer sheath, there may be greater frictional contact with the inside wall of the sheath. The increased friction may make removal of instruments difficult or impossible. That difficulty may increase the likelihood of dislodgement of the sheath. To limit frictional engagement, introducer sheaths with larger internal (and, thus, external) diameters may be used for a given procedure.

The use of larger diameter introducer sheaths is not, however, without disadvantages. For example, larger diameter introducer sheaths can create a larger hole in, e.g., an arterial wall, at the insertion site. Anti-clotting medications (often used to improve procedure outcomes by reducing the risk of unwanted blood clots forming at the treatment site) may complicate sealing of the insertion site by interfering with normal hemostasis (control of bleeding)—especially when the insertion site is larger to accommodate a larger sheath. Such complications may include, e.g., hematomas, pseudoanuerysms, and other bleeding disorders.

The use of larger introducer sheaths can also cause a tear in the vessel wall, particularly if the incision at the insertion site is too small. This is, in part, a function of anatomy because intermittent radially-oriented bands of muscle form part of the vessel wall. Between these muscle bands is relatively weaker connective tissue. The passing of the introducer sheath through the vessel wall can cause a tear or split in the connective tissue between muscle bands, causing a lateral tear in the vessel wall.

SUMMARY OF THE INVENTION

The present invention provides an introducer apparatus with a plurality of cutting edges along the outer surface of the distal end of an introducer that may preferably adapted to extend from and be withdrawn into the sheath. The cutting edges may preferably resect tissue located around the insertion site during passage of the introducer.

The cutting edges on the introducer may preferably extend along only a distal section of the introducer, that is, the cutting edges are not required to extend along the entire length of the introducer component of the apparatus. The cutting edges may preferably form incisions in a radial or "star" pattern to, e.g., cut the muscle fiber bands and allow a portion of the pressure, stretching and friction generated by the sheath to be relieved vertically (i.e., axially along the length of the vessel wall rather than radially), thus potentially reducing the likelihood of lateral (radial) tearing.

In one aspect, the present invention provides an introducer apparatus that includes a sheath having a distal end and a proximal end, a central longitudinal axis extending between the distal end and the proximal end of the sheath, a sheath lumen extending through the sheath towards the proximal end of the sheath, and a distal opening in the sheath lumen at the distal end of the sheath. The introducer apparatus may also preferably include an introducer extending out of the distal opening of the sheath along the central longitudinal axis, wherein the introducer has a blunt distal end, and wherein the introducer further includes an outer surface with three or more cutting edges extending therefrom, wherein each cutting edge of the three or more cutting edges is aligned on the outer surface of the introducer to create an incision at an insertion site.

In various embodiments one or more of the following features may be present: each cutting edge of the three or more cutting edges is aligned parallel to the central longitudinal axis; the cutting edges extend to the distal opening of the introducer; each cutting edge of the three or more cutting edges extends along only a distal section of the introducer; the blunt distal end of the introducer is oriented orthogonal to the central longitudinal axis; the introducer extends through at least a portion of the sheath lumen; the introducer includes an outer diameter that is sized to fit within the sheath lumen such that the introducer is capable of being withdrawn through the sheath lumen in the proximal direction after introduction of the introducer and the distal end of the sheath through the insertion site; the introducer includes an introducer lumen aligned along the central longitudinal axis such that the introducer and the sheath can be guided through an incision over a guidewire that passes through the insertion site; the incisions created by each cutting edge of the three or more cutting edges is aligned radially relative to the central longitudinal axis; the three or more cutting edges are evenly spaced about the central longitudinal axis; etc.

In another aspect, the present invention may provide a method of introducing a sheath to an internal body location using an introducer apparatus according to the present invention, the method including advancing the introducer and the sheath through a linear incision at an insertion site over a guidewire that passes through the incision, wherein at least one cutting edge of the three or more cutting edges resects tissue in a direction that is not aligned with the linear incision; and withdrawing the introducer in the proximal direction through the sheath lumen after advancing the introducer and the distal end of the sheath through the incision, wherein the sheath remains in position through the incision after withdrawal of the introducer.

These and other features and advantages may be described below in connection with one or more exemplary embodiments of the invention.

BRIEF DESCRIPTIONS OF THE FIGURES

DESCRIPTIONS OF EXEMPLARY
EMBODIMENTS OF THE INVENTION

In the following detailed description of some exemplary embodiments of the invention, reference is made to the accompanying figures which form a part hereof, and in which are shown, by way of illustration, specific embodiments in which the invention may be practiced. It is to be understood that other embodiments may be utilized and structural changes may be made without departing from the scope of the present invention.

Figure 1:
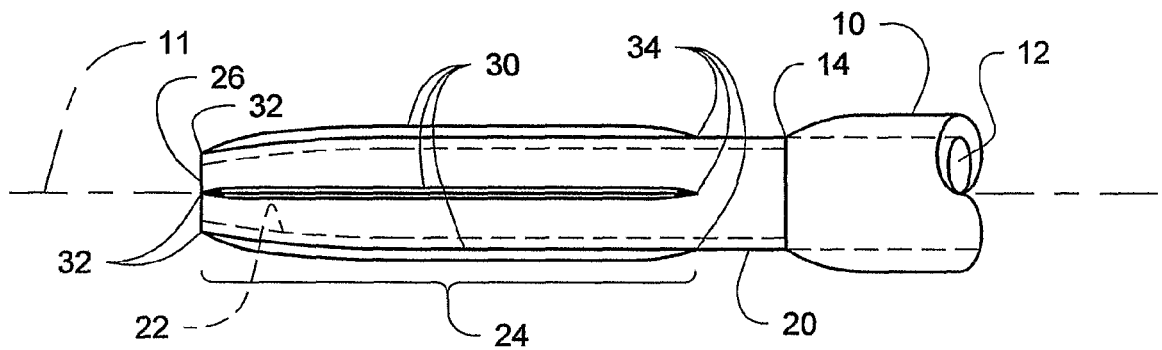
FIG. 1 is a side view of one exemplary embodiment of an introducer apparatus according to the present invention in which the introducer 20 protrudes from the distal end of the sheath 10.
Figure 2:
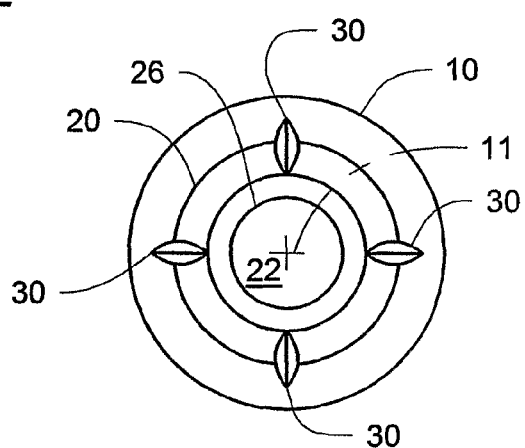
FIG. 2 is an end view of the introducer apparatus of FIG. 1 taken in the proximal direction along axis 11 (from left to right in FIG. 1).

FIG. 1 is a side view of the distal portion of one exemplary introducer apparatus that may be provided in accordance with the present invention, while FIG. 2 is a view of the apparatus taken along the longitudinal axis 11 in the proximal direction. The introducer apparatus includes a sheath 10 with an elongated body that includes a lumen 12 extending along the length of the sheath 10 with an opening at the distal end 14 of the sheath 10 and typically an opening at the proximal end (not shown) similar to conventional introducer sheaths.

The introducer apparatus also includes an introducer 20 that, in the embodiment depicted in FIGS. 1-2, extends out of or protrudes from the opening in the distal end 14 of the sheath 10. The introducer 20 includes a distal end 26 and a proximal end (not shown) similar to known devices. The introducer 20 may also taper in size proximate the distal end 26 such that the introducer 20 has a smaller diameter than the diameter of the portion of the introducer 20 located proximally of the distal end 26.

The introducer 20 also preferably includes an introducer lumen 22 extending through the introducer 20. The introducer lumen 22 may preferably be used during insertion and advancement of the introducer apparatus to guide the introducer apparatus over a wire (e.g., a guidewire or other guide device/technique) that has been previously inserted through the incision by, e.g., a needle or other device.

The introducer 20 also preferably includes cutting edges 30 each of which includes a distal end 32 proximate the distal end 26 of the introducer 20. It may be preferred that the cutting edges 30 extend to the distal opening at the distal end 26 of the introducer 20 as depicted in FIG. 1 such that distal end 32 of each cutting edge 30 be located at the distal end 26 of the introducer 20.

Although the depicted embodiment includes four cutting edges 30, it will be understood that the introducers of the present invention may include as few as three cutting edges and more than four cutting edges. The cutting edges 30 all preferably terminate at a proximal end 34 that is located within a tip section 24 of the introducer 20.

Figure 3:
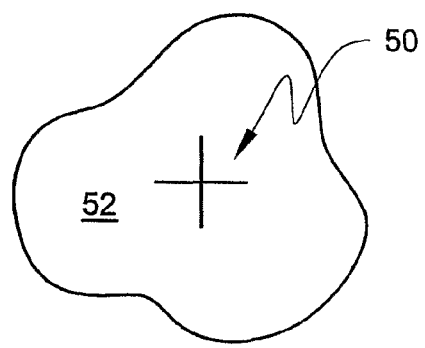
FIG. 3 depicts the incisions formed by an introducer sheath according to FIG. 1.

The cutting edges 30 may preferably be aligned along radii extending through the central longitudinal axis 11 which preferably extends through the center of the introducer 20. As a result, the cutting edges 30 preferably make a pattern of incisions that extend radially from a central point similar to the pattern of incisions 50 depicted in tissue 52 as seen in FIG. 3. It may be preferred that the cutting edges further be aligned generally parallel with the longitudinal axis 11. Further, it may be preferred that the cutting edges 30 be evenly spaced about the longitudinal axis 11 as depicted in, e.g., FIG. 2.

The distal end 26 of the introducer 20 is, in the embodiment depicted in FIGS. 1-2, preferably blunt. In other words, the distal end 26 of the introducer 20 may preferably not include any cutting edges or surfaces. Further, the distal end 26 may preferably be formed by a surface or edge that is generally orthogonal to the central longitudinal axis 11. In addition, the distal end 14 of the heath 10 may also preferably be blunt (without cutting edges or surfaces and also formed by a surface or an edge that is also generally orthogonal to the central longitudinal axis 11). Because of their blunt ends, the introducer 20 and its accompanying sheath 10 may be designed for insertion into an incision that is already present in tissue (e.g., a vessel wall, etc.). The pre-existing incision may preferably be in the form of a single straight line incision as disclosed in FIGS. 1-2 of U.S. Pat. No. 6,921,387 B1 (Camrud). As discussed above, potential advantages of the present invention include the ability to expand a linear incision to allow insertion of a larger instrument while limiting tearing of tissue that may cause a variety of problems.

The introducer apparatus of the present invention may preferably be inserted when the introducer 20 extends from the distal end 14 of the sheath 10 as seen in, e.g., FIG. 1. In that arrangement, the introducer 20 with the cutting edges 30 enters the insertion site first, allowing the cutting edges to form the desired stress-relieving incision patterns discussed herein. The larger diameter sheath 10, which follows the exposed portion of the introducer 20, can then pass through the insertion site. After it is in position with the sheath 10 passing through the insertion site, the introducer 20 may preferably be withdrawn in the proximal direction into the sheath 10 to allow full access to the sheath lumen 12 for other instruments and devices to pass.

In other embodiments and methods, however, the introducer 20 may remain in the position depicted in FIG. 1, with other instruments and devices passing through the lumen 22 in the introducer 20.

The materials used to construct introducer apparatus of the present invention may preferably be those materials suitable for use in medical devices, e.g., metals, polymers, composite materials, etc. In addition, it may be preferred that the introducer apparatus of the present invention have sufficient flexibility to follow a desired path through tissue. In some instances, for example, it may be preferred that the sheath and the introducer be capable of flexibly forming a curve with a radius of at least 10 centimeters without significantly reducing the opening of the lumen in the sheath and/or introducer.

Some exemplary dimensions for the various components of the introducer apparatus of the present invention may be an outer diameter (for the sheath 10) of from 1 millimeter (mm) to 30 mm or more. The length of the sheath may be, e.g., 4 centimeters (cm) to 30 cm or more. It may be preferred that the introducer 20 be longer than the sheath to allow the distal end section of the introducer (with cutting edges) to extend past the distal end of the sheath.

As used herein and in the appended claims, the singular forms "a," "and," and "the" include plural referents unless explicitly limited to the singular form or the context clearly dictates otherwise.

All references and publications cited herein are expressly incorporated herein by reference in their entirety into this disclosure. Illustrative embodiments of this invention are discussed and reference has been made to possible variations within the scope of this invention. These and other variations and modifications in the invention will be apparent to those skilled in the art without departing from the scope of the invention, and it should be understood that this invention is not limited to the illustrative embodiments set forth herein. Accordingly, the invention is to be limited only by the claims provided below and equivalents thereof.

The invention claimed is:

1. A method of introducing a sheath to an internal body location, the method comprising:
    providing an introducer apparatus; that comprises:
        a sheath comprising a distal end and a proximal end, a central longitudinal axis extending between the distal end and the proximal end of the sheath, a sheath lumen extending through the sheath towards the proximal end of the sheath, and a distal opening in the sheath lumen at the distal end of the sheath; and
        an introducer extending out of the distal opening of the sheath along the central longitudinal axis, wherein the introducer comprises a blunt distal end, and wherein the introducer further comprises an outer surface that comprises three or more cutting edges extending therefrom, wherein each cutting edge of the three or more cutting edges is aligned on the outer surface of the introducer;
    advancing the introducer and the sheath through a linear incision at an insertion site over a guidewire that passes through the incision, wherein at least one cutting edge of the three or more cutting edges resects tissue at the insertion site in a direction that is not aligned with the linear incision;
    withdrawing the introducer in the proximal direction through the sheath lumen after advancing the introducer and the distal end of the sheath through the incision, wherein the sheath remains in position through the incision after withdrawal of the introducer.

2. A method according to claim 1, wherein each cutting edge of the three or more cutting edges is aligned parallel to the central longitudinal axis.

3. A method according to claim 1, wherein the cutting edges extend to the distal end of the introducer.

4. A method according to claim 1, wherein each cutting edge of the three or more cutting edges extends along only a distal section of the introducer.

5. A method according to claim 1, wherein the blunt distal end of the introducer is oriented generally orthogonal to the central longitudinal axis.

6. A method according to claim 1, wherein the introducer extends through at least a portion of the sheath lumen.

7. A method according to claim 1, wherein the introducer comprises an outer diameter that is sized to fit within the sheath lumen, and wherein the method further comprises withdrawing the introducer through the sheath lumen in the proximal direction after introduction of the introducer and the distal end of the sheath through the insertion site.

8. A method according to claim 1, wherein the introducer comprises an introducer lumen aligned along the central longitudinal axis such that the introducer and the sheath can be guided through an incision over a guidewire that passes through the insertion site.

9. A method according to claim 1, wherein the incisions created by each cutting edge of the three or more cutting edges is aligned radially relative to the central longitudinal axis.

10. A method according to claim 1, wherein the three or more cutting edges are evenly spaced about the central longitudinal axis.

11. A method according to claim 1, wherein the linear incision is made in a blood vessel wall.

12. A method of introducing a sheath to an internal body location, the method comprising:
    providing an introducer apparatus that comprises:
        a sheath comprising a distal end and a proximal end, a central longitudinal axis extending between the distal end and the proximal end of the sheath, a sheath lumen extending through the sheath towards the proximal end of the sheath, and a distal opening in the sheath lumen at the distal end of the sheath; and
        an introducer extending out of the distal opening of the sheath along the central longitudinal axis, wherein the introducer comprises a blunt distal end, and wherein the introducer further comprises an outer surface that comprises three or more cutting edges extending therefrom, wherein each cutting edge of the three or more cutting edges is aligned on the outer surface of the introducer;
    advancing the introducer and the sheath through an insertion site over a guidewire that passes through the insertion site, wherein at least one cutting edge of the three or more cutting edges resects tissue at the insertion site;
    withdrawing the introducer in the proximal direction through the sheath lumen after advancing the introducer and the distal end of the sheath through the insertion site, wherein the sheath remains in position through the insertion site after withdrawal of the introducer.

13. A method according to claim 12, wherein the insertion site is in a blood vessel wall.

14. A method according to claim 12, wherein each cutting edge of the three or more cutting edges is aligned parallel to the central longitudinal axis.

15. A method according to claim 12, wherein the cutting edges extend to the distal end of the introducer.

16. A method according to claim 12, wherein each cutting edge of the three or more cutting edges extends along only a distal section of the introducer.

17. A method according to claim 12, wherein the blunt distal end of the introducer is oriented generally orthogonal to the central longitudinal axis.

18. A method according to claim 12, wherein the introducer extends through at least a portion of the sheath lumen.

19. A method according to claim 12, wherein the introducer comprises an outer diameter that is sized to fit within the sheath lumen, and wherein the method further comprises withdrawing the introducer through the sheath lumen in the proximal direction after introduction of the introducer and the distal end of the sheath through the insertion site.

20. A method according to claim 12, wherein the incisions created by each cutting edge of the three or more cutting edges is aligned radially relative to the central longitudinal axis.

* * * * *